United States Patent [19]

Lin

[11] Patent Number: 5,522,892
[45] Date of Patent: Jun. 4, 1996

[54] BREAST AUGMENTATION DEVICE

[76] Inventor: Chin-Lung Lin, 2F, No. 180, Section 3, Jong Shiaw E. Road, Taipei, Taiwan

[21] Appl. No.: 411,506

[22] Filed: Mar. 28, 1995

[51] Int. Cl.⁶ ............................... A61F 2/52; A41C 3/00; A41C 3/10
[52] U.S. Cl. .................. 623/7; 450/39; 450/57; 450/55
[58] Field of Search ............................. 623/7, 8, 11, 17; 450/39, 40, 41, 42, 53, 54, 55, 56, 57; 2/267

[56] References Cited

U.S. PATENT DOCUMENTS

| | | | |
|---|---|---|---|
| 146,805 | 1/1874 | Cox | 623/7 |
| 401,028 | 4/1889 | Greene | 450/39 |
| 2,066,503 | 1/1937 | Wiggers | 623/7 |
| 2,696,005 | 12/1954 | Schaumer | 623/7 |
| 3,494,365 | 2/1967 | Beals | 450/55 |
| 3,896,506 | 7/1975 | Hankin et al. | 623/7 |
| 4,258,442 | 3/1981 | Eberl | 450/41 |
| 4,264,990 | 5/1981 | Hamas | 623/8 |

Primary Examiner—Debra S. Brittingham
Attorney, Agent, or Firm—Bacon & Thomas

[57] ABSTRACT

A breast augmentation device made from flexible rubber, having a breast-shaped front part and a hollow, rounded rear part for covering over the breast, wherein the rear part has a plurality of elongated grooves with vent holes and a plurality of elongated ribs, each elongated groove having at least one end perpendicularly connected to the periphery of the orifice of the hollow, rounded rear part, each elongated rib having a center portion and two opposite ends extended from the center portion and perpendicularly connected to the periphery of the orifice, the height of each elongated rib reducing gradually from the respective center portion toward the respective opposite ends.

6 Claims, 4 Drawing Sheets

BREAST AUGMENTATION DEVICE

BACKGROUND OF THE INVENTION

The present invention relates to an artificial breast addition to a bodily part worn to enhance appearance, and relates more specifically a breast-shaped rubber cup of thickness gradually reducing from the center toward the border, used to pad a swimming costume, brassiere, undergarment. The falsie has elongated ribs and elongated grooves on the back side thereof and vent holes through the elongated grooves.

A variety of cup paddings and falsies have been developed and intensively used by women to pad brassieres for wearing over the breasts to enhance the appearance of the front upper part of the body. For example, BRASSIERE WITH HALF-CUP PADDINGS of Chinese Patent Application No. 6323174 (Publication No. 20712) teaches the use of a flexible cotton or sponge support to pad the brassiere. However, a brassiere of this type is not comfortable in use because the support stops air from circulating through the brassiere. FALSIE of Chinese Patent Application No. 6320504 (Publication No. 16692) teaches the use of cup-like water bags to pad the brassiere. Chinese Patent Application No. 6422120 (Publication No. 22012) discloses another structure of falsie which is molded from rubber and supported in shape by a supporting device, defining a plurality of water chambers respectively filled up with a fluid. This structure of falsie will collapse if the supporting device is damaged or not properly arranged in position. Furthermore, this structure of falsie prohibits the circulation of air through the brassiere, causing discomfort.

SUMMARY OF THE INVENTION

The present invention has been accomplished under the circumstances in view. It is therefore an object of the present invention to provide a falsie for padding the brassiere, swimming costume, etc. which greatly enhances the appearance of the front upper part of the user. It is another object of the present invention to provide a falsie for padding the brassiere which has back spaces for ventilation. It is still another object of the present invention to provide a brassiere which is comfortable in use.

According to one aspect of the present invention, the falsie is integrally molded from rubber or silicon rubber.

According to another aspect of the present invention, the falsie comprises a breast-shaped front part, and a hollow, rounded rear part defining a circular orifice for covering over the breast, wherein the rear part has a plurality of elongated grooves with vent holes and a plurality of elongated ribs, each elongated groove having at least one end perpendicularly connected to the periphery of the orifice, each elongated rib having a center portion and two opposite ends extended from the center portion and perpendicularly connected to the periphery of the orifice. When the falsie is worn to the breast, the elongated grooves and the vent holes impart spaces for ventilation.

According to still another aspect of the present invention, the height of each elongated rib reduces gradually from the respective center portion toward the respective opposite ends, therefore the falsie can be smoothly and comfortably covered over the breast.

BRIEF DESCRIPTION OF THE DRAWINGS

The present invention will now be described by way of example only with reference to the annexed drawings, in which.

DETAILED DESCRIPTION OF THE PREFERRED EMBODIMENT

Figure 1:
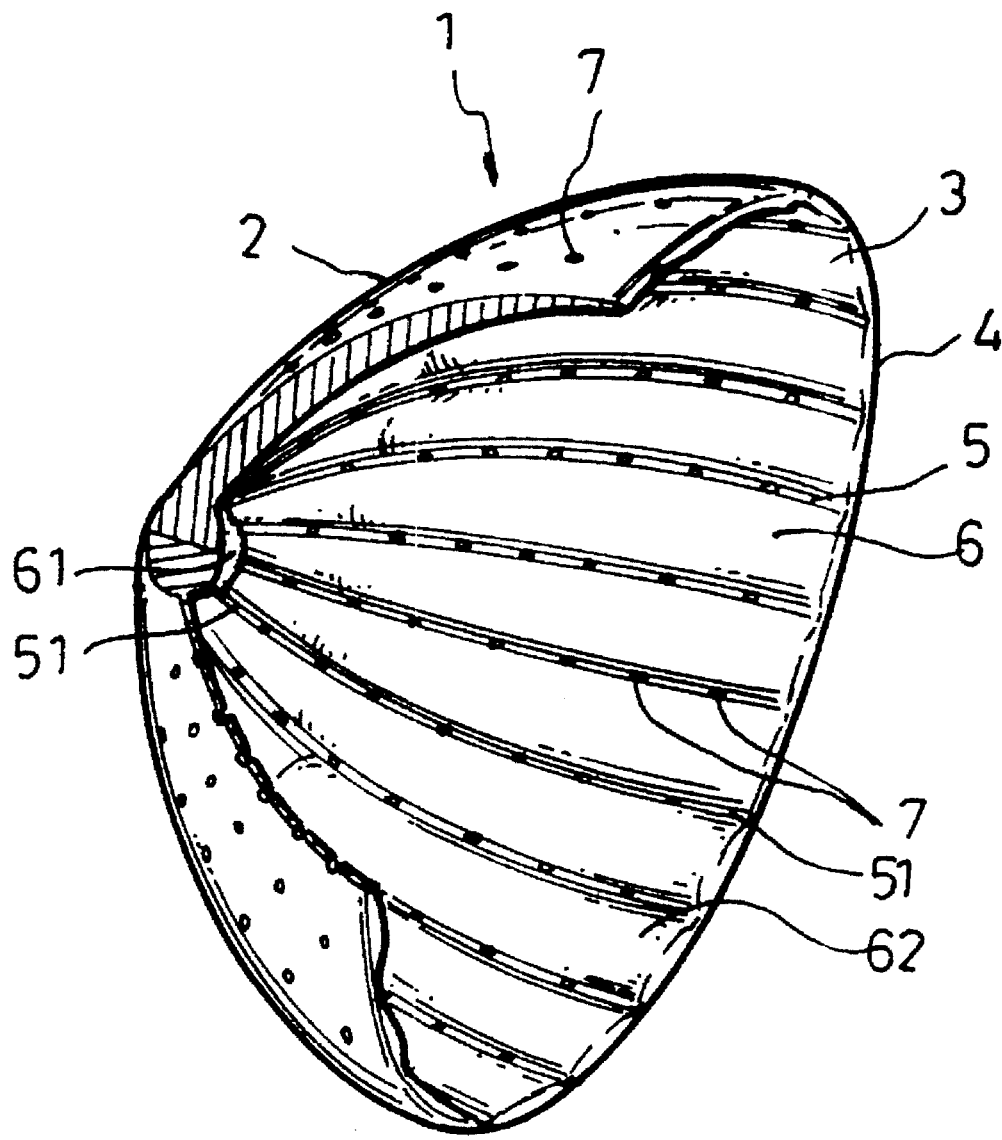
FIG. 1 is a cutaway view of a falsie according to the present invention.

Referring to FIGS. 1, a falsie, referenced by 1, is molded from flexible rubber, having a breast-shaped front part 2 and a hollow, rounded rear part 3 for covering over the breast. The rear part 3 comprises a circular orifice 4, a plurality of elongated grooves 5, a plurality of elongated ribs 6, and a plurality of vent holes 7 through the elongated grooves 5.

Referring to FIG. 1 again, the hollow, rounded rear part 3 has a plurality of elongated grooves 5 and a plurality of elongated ribs 6, wherein each elongated groove 5 has one end 51 perpendicularly connected to the periphery of the orifice 4; the elongated ribs 6 are identical, each comprising a center portion 61 respectively linked together and two opposite end portions 62 respectively and perpendicularly connected to the periphery of the orifice 4. The height of each elongated rib 6 gradually reduces from the center portion 61 toward the end portions 62.

Figure 2:
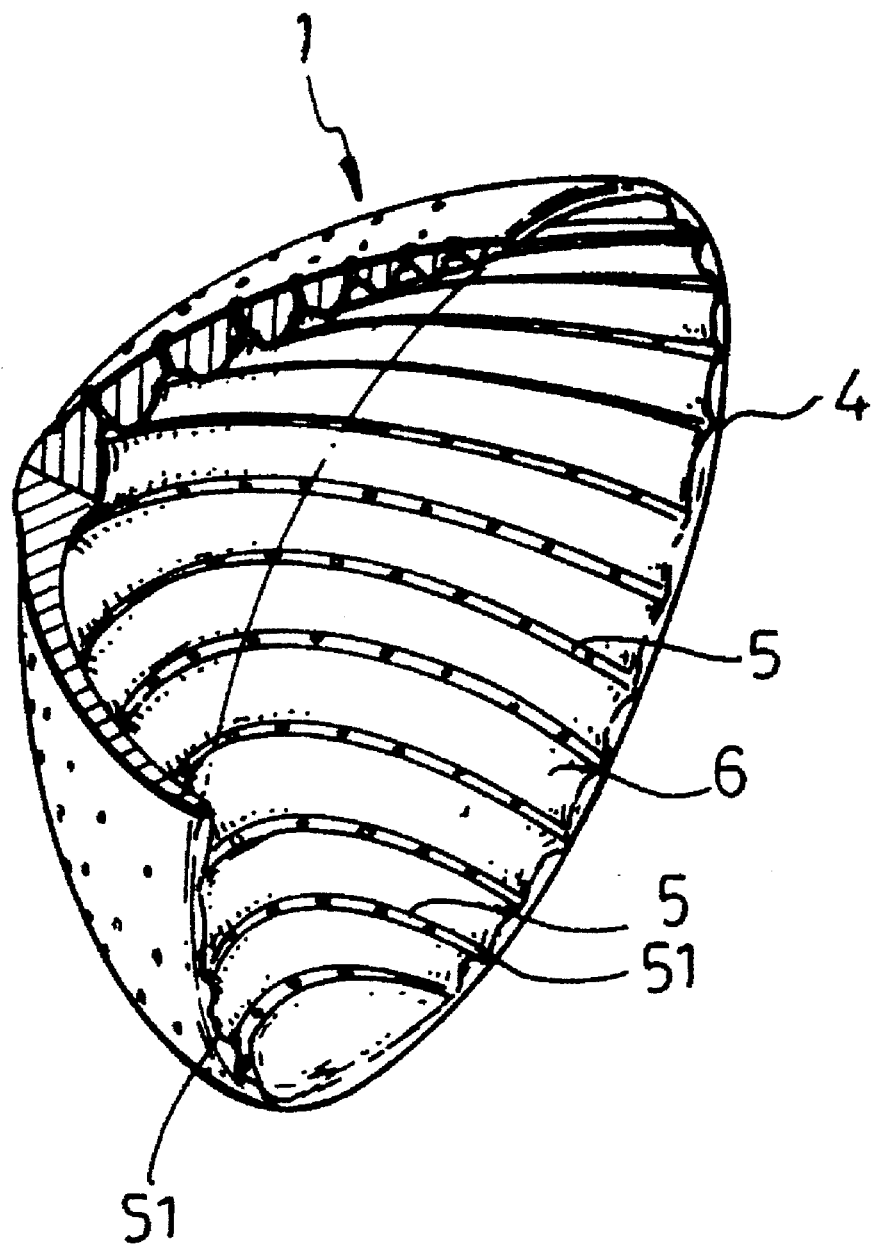
FIG. 2 is a cutaway view of an alternate form of the falsie according to the present invention.

FIG. 2 shows an alternate form of the present invention in which the elongated grooves 5 and the elongated ribs 6 are alternatively arranged in parallel with one another, each elongated groove 5 has both ends 51 respectively and perpendicularly connected to the periphery of the orifice 4.

Figure 3:
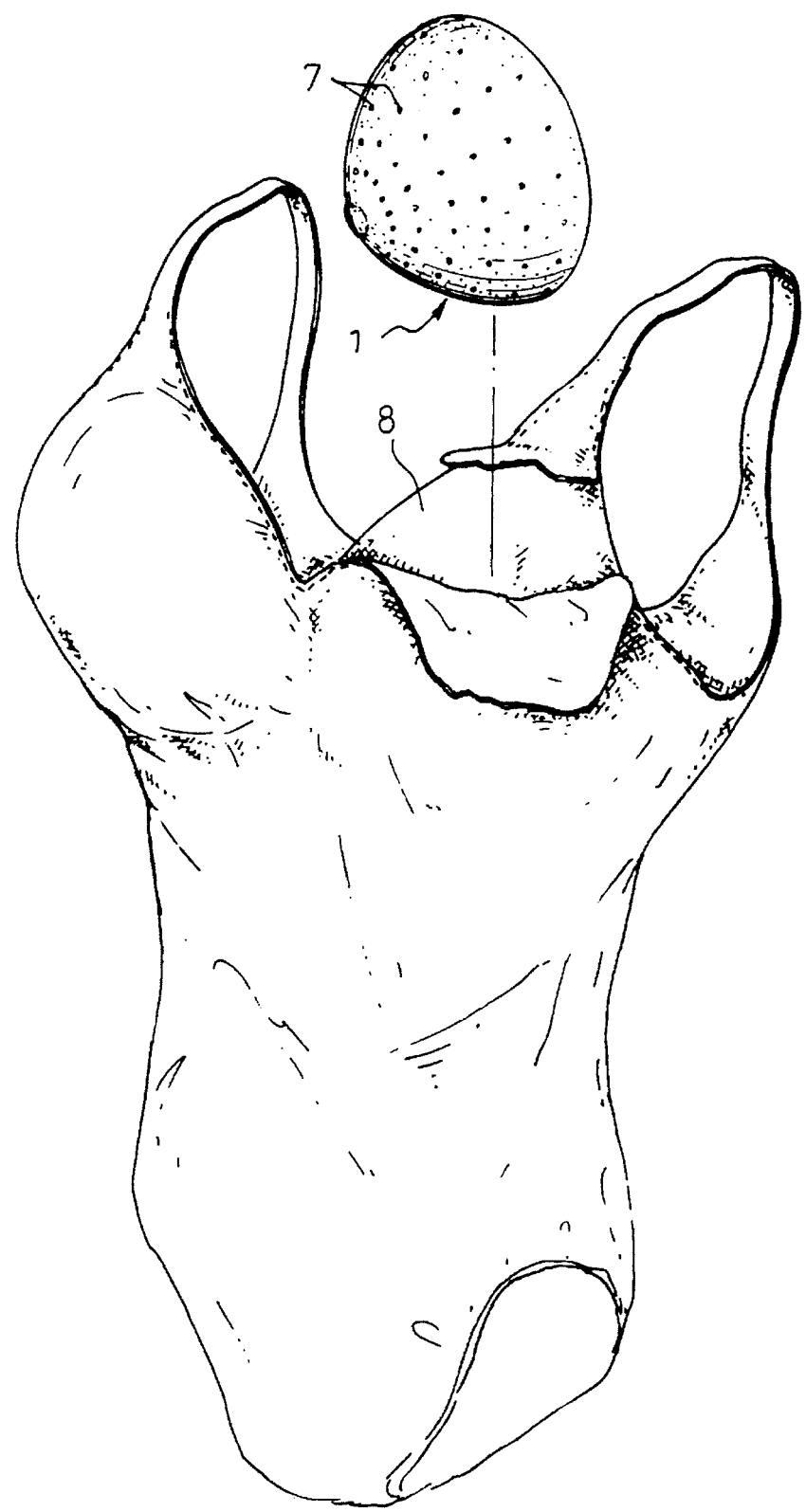
FIG. 3 shows the positioning of the falsie of the present invention in a swimming costume.
Figure 4:
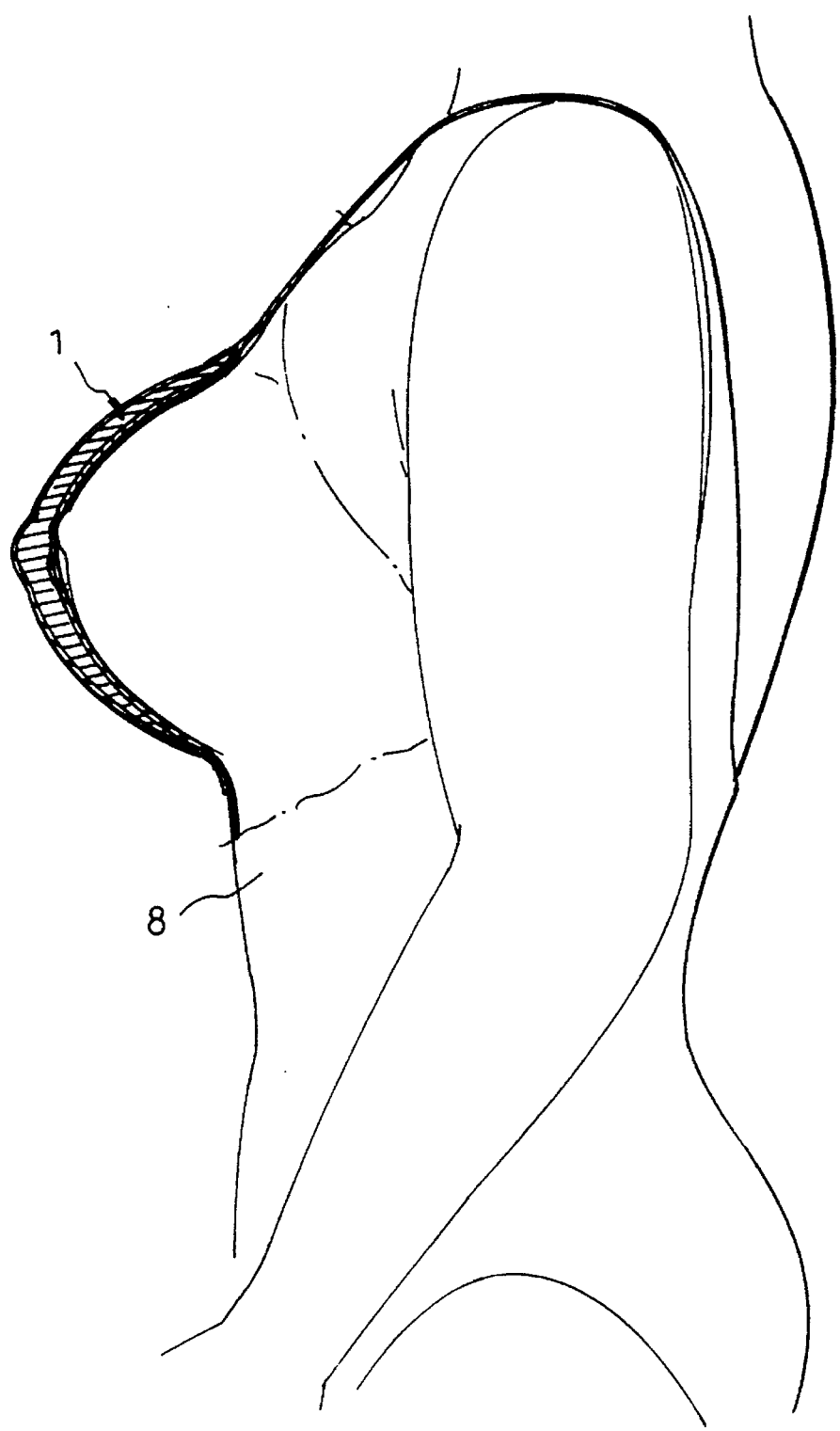
FIG. 4 shows the falsie of FIG. 3 fastened to the swimming costume.

Referring to FIGS. 3 and 4, when the falsie 1 is fastened to the swimming costume over the breast area, it enhances the appearance of the user's upper front part. As the periphery of the orifice of the falsie 1 is relatively thinner, the falsie 1 can be smoothly and comfortably covered over the user's breast. When the user walks, the falsie 1 will be forced to oscillate and to imitate the waving of the breast. Furthermore, the elongated grooves and the vent holes 7 on the elongated grooves impart spaces for ventilation; the elongated ribs massage the breast when the falsie 1 is waved.

It is to be understood that the drawings are designed for purposes of illustration only, and are not intended as a definition of the limits and scope of the invention disclosed.

What is claimed is:

1. A breast augmentation device comprised of a breast-shaped front part, and a hollow, rounded rear part defining an interior surface terminating to a peripheral circular orifice for receiving therein and covering over the breast, wherein the interior surface comprises a plurality of elongated grooves for dissipating heat from the breast and a plurality of elongated ribs, each elongated groove having two opposite ends, at least one end of each elongated groove being perpendicularly connected to the periphery of said circular orifice, each elongated rib comprising a center portion and two opposite end portions extended from said center portion and perpendicularly connected to the periphery of said circular orifice, and the height of each elongated rib reducing gradually from the respective center portion toward the respective opposite ends.

2. The breast augmentation device of claim 1 wherein said elongated ribs are identical, having the respective center portions respectively linked together.

3. The breast augmentation device of claim 1 wherein said elongated ribs are arranged in parallel at different elevations.

4. The breast augmentation device of claim 1 wherein said rear part comprises a plurality of vent holes through said elongated grooves.

5. The breast augmentation device of claim 1 which is molded from rubber.

6. The breast augmentation device of claim 1 which is molded from silicon rubber.

* * * * *